(12) United States Patent
Willing et al.

(10) Patent No.: US 8,594,143 B2
(45) Date of Patent: Nov. 26, 2013

(54) LASER DIODE STRUCTURE WITH INTEGRATED TEMPERATURE-CONTROLLED BEAM SHAPING ELEMENT AND METHOD FOR GAS DETECTION BY MEANS OF A LASER DIODE STRUCTURE

(75) Inventors: Bert Willing, Blonay (CH); Rui Protasio, Lucern (CH); Mathieu Gaillard, Lausanne (CH)

(73) Assignee: Axetris AG, Kagiswil (CH)

( * ) Notice: Subject to any disclaimer, the term of this patent is extended or adjusted under 35 U.S.C. 154(b) by 0 days.

(21) Appl. No.: 12/628,578

(22) Filed: Dec. 1, 2009

(65) Prior Publication Data
US 2011/0110390 A1    May 12, 2011

(30) Foreign Application Priority Data
Nov. 6, 2009 (EP) .................................. 09013934

(51) Int. Cl.
*H01S 3/04*        (2006.01)
(52) U.S. Cl.
USPC ....... 372/36; 372/43.01; 372/50.23; 372/101; 372/107
(58) Field of Classification Search
USPC ........................................................... 372/36
See application file for complete search history.

(56) References Cited

U.S. PATENT DOCUMENTS

| | | | | |
|---|---|---|---|---|
| 4,995,050 A | * | 2/1991 | Waarts et al. | 372/95 |
| 5,062,117 A | * | 10/1991 | Anthon et al. | 372/75 |
| 5,081,639 A | * | 1/1992 | Snyder et al. | 372/101 |
| 5,883,737 A | * | 3/1999 | Fujikawa et al. | 359/345 |
| 6,040,934 A | * | 3/2000 | Ogusu et al. | 398/139 |
| 6,353,225 B1 | | 3/2002 | Strzoda et al. | |
| 6,943,967 B2 | * | 9/2005 | Zetterlund | 359/819 |
| 2002/0003819 A1 | * | 1/2002 | Kimura et al. | 372/36 |
| 2002/0093024 A1 | | 7/2002 | Lee et al. | |

(Continued)

FOREIGN PATENT DOCUMENTS

CN          1623109 A     6/2005
CN       101300475 A    11/2008

(Continued)

OTHER PUBLICATIONS

European Search Report for corresponding Application No. 09 01 3934 dated Dec. 11, 2009.

*Primary Examiner* — Xinning Niu
(74) *Attorney, Agent, or Firm* — Renner, Otto, Boisselle & Sklar, LLP

(57) ABSTRACT

The invention relates to a laser diode structure, specifically for use in gas detection, with a hermetically sealed housing with electrical connections having a bottom and a window. A laser diode chip and a temperature control system for the laser diode chip are provided in the housing. A thermo element in the form of a Peltier element forms the temperature control system, and is connected via a lower flat surface to the bottom of the housing and via an upper flat surface to the laser diode chip, with a temperature-controlled beam shaping element as collimator provided between the laser diode chip and the window of the housing that acts on a laser beam emerging from a laser aperture of the laser diode chip before it passes through the window. The beam shaping element is in contact with the laser diode chip and is preferably connected via a boundary surface to the laser aperture with surface-to-surface contact or adhesively, or is made in one piece together with the laser aperture.

10 Claims, 1 Drawing Sheet

(56) References Cited

U.S. PATENT DOCUMENTS

2004/0218636 A1* 11/2004 Kashima et al. .................. 372/9
2005/0083568 A1    4/2005 Nakae et al.
2006/0227844 A1* 10/2006 Guenter ........................ 372/101
2007/0159773 A1*  7/2007 Deng et al. .................... 361/600
2008/0232422 A1*  9/2008 Sutton et al. .................. 372/101

FOREIGN PATENT DOCUMENTS

| | | |
|---|---|---|
| DE | 197 17 145 | 10/1998 |
| DE | 101 08 873 | 7/2002 |
| EP | 1 207 599 | 5/2002 |
| EP | 1 411 601 A1 | 3/2004 |
| EP | 1 783 481 | 5/2007 |

\* cited by examiner

LASER DIODE STRUCTURE WITH INTEGRATED TEMPERATURE-CONTROLLED BEAM SHAPING ELEMENT AND METHOD FOR GAS DETECTION BY MEANS OF A LASER DIODE STRUCTURE

CROSS-REFERENCE TO RELATED APPLICATION

The present application claims priority under 35 USC §119 to European Patent Application No. 09 013 934.6 filed Nov. 6, 2009, the entire disclosure of which is incorporated herein by reference.

TECHNICAL FIELD OF THE INVENTION

The invention relates to a laser diode structure, specifically for use in gas detection, with a hermetically sealed housing with electrical connections having a bottom and a window, with a laser diode chip and a temperature control system for the laser diode chip being provided in the housing, and with an optical beam shaping element that collimates a laser beam emerging from a laser aperture of the laser diode chip prior to its passage through the window being provided between the laser diode chip and the window of the housing. In addition, the invention relates to a method for gas detection by means of a laser diode structure.

DESCRIPTION OF THE RELATED ART

There is a great need for cost-efficient, reliable, and highly sensitive gas sensors due to a large number of applications in the sectors of security, comfort, and environmental protection. With known gas sensors, the detection of gases is frequently accomplished by making use of absorption spectroscopy. With this technology, a beam of light, for example a laser beam of a certain frequency that is strongly absorbed by the gas for which the gas sensor is designed, is directed through a gas or a mixture of gases. The degree of absorption of the light beam is then used as an indicator for the concentration of the gas to be detected. For gas detection, spectrally single-mode laser diodes are especially well suited that, today, can be manufactured also for operating temperatures of up to 100° C.

As prior art, the German patent disclosure DE 197 17 145 C2 disclosed a method that, by means of a mono-mode DFB laser diode, and by exploiting the tunability of this diode regarding the emission wave length via the operating temperature of the diode, picks up and/or scans parts of the spectra of gases to be measured and, in doing so, detects the gases by means of their characteristic spectral lines and then determines the concentration of the gas. In the general application of the measuring method, the operating temperature of the laser is commonly kept constant by means of a thermoelectric cooler (Peltier element), and the tuning of the wave length is accomplished by means of a variation of the operating voltage of the laser diode. With tunable laser gas detection (TDLS) in particular, high detection sensitivity requires that the laser radiation emitted by the laser diode semiconductor chip emerges from the laser diode with a minimum of interference phenomena. Such interference may be caused by reflections of the laser light on interior surfaces of the housing of the laser diode acting like mirrors, or on the inner or outer surface of the window of the laser diode, or by similar surfaces of the components arranged in the housing.

In laser absorption spectroscopy, after passing through a measuring section containing a gas or a mixture of gases, the absorption of the light emitted by the laser diode is measured by means of a detector, for example a light-sensitive semiconductor element or a thermal sensor element, and the received signal is fed into a signal analyzer. During the analysis, the signal analyzer is capable of separating constant interference patterns from the received signal without problems. In contrast, changing interference patterns cannot be completely eliminated during the analysis of the received signal, so that the noise of the laser beam receiver is significantly increased which causes the detection sensitivity for the gases to be detected to decrease. Changing interference patterns are usually caused by temperature influences, on or in the housing of the laser diode structure, that cannot be eliminated and that cause a change of the length of the optical path of the laser light in the housing of the laser diode structure. In cases where, for example, a microlens as collimator for the laser beam is provided in the laser diode structure between the laser diode chip attached to the bottom of the housing and the window of the housing, reflections of the laser light emerging from a laser aperture of the laser diode chip will, naturally, also occur at those boundary surfaces of the microlens that are oriented transversely to the laser beam. Like the corresponding reflections of the laser beam on the housing window, these reflections may also lead to interference patterns that are superimposed on other possibly occurring interference patterns. The interference patterns caused by the microlens may also change dependent on the temperature, and will therefore have a negative effect on the resolution of the gas sensor.

SUMMARY OF THE INVENTION

The invention addresses the problem of proposing a method for improving the sensitivity of a gas sensor by avoiding or greatly reducing interference phenomena of the laser beam when it emerges from a closed, hermetically sealed housing of a laser diode structure.

According to the invention, this problem is solved by a laser diode structure and method for reducing interference phenomena of a laser diode structure.

In the laser diode structure according to the invention, preferably for use with a device for gas detection, the window of the housing is inclined relative to the center axis of the laser beam in such a way that reflections of the laser beam in the direction of the laser diode structure that may occur at the window will miss the laser aperture of the laser diode chip. The azimuth angle of the window inclination has a fixed relation to the polarization vector of the laser beam in that the polarization vector is in the plane of incidence of the window. The window, located opposite the bottom with the laser diode chip, may be arranged in a parallel or inclined configuration, or may be appropriately arranged on side walls of the housing that extend away from the bottom. In terms of transmission and reflection, the laser beam hitting the inside of the window facing the optical beam shaping element behaves in accordance with the Brewster angle known from optical science. The beam shaping element is in physical contact with the laser diode chip and has a defined temperature condition in relation to the laser diode chip. The contact with the laser diode chip may be direct or indirect and permits a certain thermal transfer between the laser diode chip and the beam shaping element. The laser diode chip and the beam shaping element may be manufactured together as one piece, may be manufactured separately and connected to each other later, or the beam shaping element may be formed on the laser diode chip so that a close physical contact between the laser diode chip and the beam shaping element is achieved.

Preferably, a lens is used as beam shaping element. Instead of a lens, the beam shaping element may also consist of a concave mirror or a diffractive optical element or some other suitable optical element. In a preferred embodiment of the invention, the optical beam shaping element is provided directly on the laser diode chip and is preferably connected with a boundary surface to the laser aperture of the laser diode chip. It may be made of a non-deformable solid material, for example glass, or of a resilient solid material, for example plastic, or of a liquid material, for example oil, all with a suitable refractory index. With a lens made of solid material, the connection is preferably of a surface-to-surface contact type, and is of adhesive type with a lens made of liquid material. The beam shaping element is adjusted so that the laser aperture is preferably located at its focal spot. As surface-to-surface contact type connections, all types of permanent connections are included where the partners of the connection are held together by atomic or molecular forces, and which can only be separated by destroying the means of connection.

The beam shaping element and the laser diode chip always have the same temperature due to a temperature control system with an appropriate temperature control. This can be achieved with a Peltier element, an actual heating system, or a combination of heating system and Peltier element. In this way, especially the laser aperture of the laser diode chip and the boundary surface of the beam shaping element associated with the aperture have a uniform temperature. With surface-to-surface contact type connections, due to the identical temperature of the laser diode chip and of the lens or the concave mirror, no uncontrollable mechanical stresses will occur that might impair the reliability of the laser diode structure. Due to the connection, without spacing, of the laser aperture and the beam shaping element, the danger of a reflection of part of the laser light of the laser beam on the boundary surface of the beam shaping element that faces the laser aperture is significantly reduced.

Preferably, the beam shaping element, for example the lens, is manufactured as a separate component and is attached to the laser aperture by means of an adhesive agent. The adhesive agent is provided as a homogeneous layer between the laser aperture and the lens. When crossing from the laser aperture to the adhesive agent layer, and from the adhesive agent layer to the boundary surface of the lens, the light waves of the laser beam are refracted in accordance with Snell's law. Snell's law says that light waves change their direction when crossing from a transparent medium with a certain phase velocity to a different transparent medium with a different phase velocity. It specifies in which direction the wave is deflected. In each medium, the laser light moves with a propagation speed that depends on the refractory index of the medium. The refractory index indicates the ratio of the phase velocity of light in a vacuum to the phase velocity of light in the medium. It is well-known that the refractory index of an adhesive agent layer, for example a layer of glue or an adhesive layer consisting of a gel or a liquid, is considerably closer to the refractory index of a lens than the refractory index of an optically thinner glass so that, when crossing from the laser diode chip to the superimposed and preferably glued beam shaping element, the laser light is refracted much less than if there were no adhesive layer between the laser aperture and the associated boundary surface of the beam shaping element.

The lens may also be connected to the laser aperture by means of a liquid. Ideally, the liquid has a refractory index that corresponds to the refractory index of the material of the optical beam shaping element. As an alternative, a lens, for example a microlens consisting of a liquid material with a suitable surface tension and a suitable refractory index may be used for the laser diode structure. Here, the liquid material forming the microlens may be applied directly to the laser aperture of the laser diode chip.

In order to prevent stray light in the housing of the laser diode structure due to bending of the laser beam at the transition from the laser diode chip to the beam shaping element, where such stray light can be reflected back in the direction of the laser aperture, parallel to the laser beam emerging from the laser diode chip, it is an advantage if the boundary surfaces of the beam shaping element and of the laser aperture of the laser diode chip are uniform in terms of shape and size. Then, the aperture angle of the laser beam emerging from the laser aperture corresponds to an aperture of the beam shaping element. It is obvious that the boundary surface of the beam shaping element facing the laser aperture may also be made larger than the laser aperture of the laser diode chip, and that the shape of the boundary surface may also deviate from the shape of the laser aperture, as long as it completely covers the laser aperture.

It proved to be especially advantageous to select an adhesive agent for connecting the beam shaping element to the laser aperture that has a refractory index that corresponds to that of the beam shaping element. By the uniform refractory index of the adhesive agent layer and the beam shaping element, the compound system consisting of laser diode chip, adhesive agent layer, and beam shaping element is reduced to a single light-refracting boundary surface between these. The effective boundary surface is located between the laser aperture and the adhesive agent layer. The boundary surface of the beam shaping element facing the laser diode chip and the adhesive agent layer is suppressed so that, from its emergence from the laser diode chip until it emerges from the beam shaping element, the laser beam is refracted only a single time at the transition between the laser aperture and the adhesive agent. This also eliminates a possible reflection surface for the laser light in the housing of the laser diode structure.

In another preferred embodiment of the invention, the beam shaping element is a microlens shaped from a polymer or Sol gel that is applied directly to the laser aperture of the laser diode chip. The application and the curing is accomplished with methods commonly used in the industry and therefore well-known to a person skilled in the art. Here, an adhesive agent layer between the microlens and the laser diode chip is not required. The polymer or Sol gel connects directly to the laser aperture or the laser diode chip by means of surface-to-surface contact.

In the discussion of the invention, 'lens' in principle means an optically effective component with two opposite light-refracting surfaces that has a collimating effect and generates parallel beams from the laser light emerging from the laser diode chip. Materials that are transparent to laser light like glass, crystals, or some special plastic materials are suitable lens materials for the microlens. The refractory index of the lens may be constant in, or transverse to the direction of the axis of the lens, or may vary at a steady rate. In any case, it is a lens that is able to parallelize the beam of a light source located in its focal spot, specifically a laser light source. Preferably, as lens for the laser diode structure according to the invention, a spherical, a dome-shaped, or a rod-shaped, spherically or aspherically convex microlens or a cylindrical GRIN (Gradient Index) lens is used.

Ideally, the microlens or the GRIN lens has a plane boundary surface associated with the laser aperture. In principle, concave boundary surfaces are also possible if they are leveled by the adhesive layer. With the microlens specified above, the laser light moves in a straight line in the lens due to the homogeneous refractory index of the lens material while, with a GRIN lens, it moves along a curved path in the lens due to the inhomogeneous refractory index. In a GRIN lens, there usually is a square-law decrease of the refractory index with the distance to the center axis (parabola function). A rod made of such a material acts like a common convergent lens but usually has plane surfaces at the light entry and light exit sides. This simplifies the assembly, the miniaturization, and the connection to the subsequent optical elements.

In an advantageous embodiment of the invention, the optical axis of the beam shaping element is offset relative to the center axis of the laser aperture. The lens or the mirror is positioned not precisely centered above the laser aperture but offset by several 10 μm relative to the axis of the laser aperture. This, of course, requires that the aperture, formed by the boundary surface, of a beam shaping element implemented as a microlens is made larger by at least the amount of the offset than the laser aperture of the laser diode chip. In contrast, with a beam shaping element implemented as a GRIN lens, the aperture of the microlens is arranged concentrically to the laser aperture as a matter of practicality, with the boundary surface that faces away from the laser aperture advantageously being sloped.

In order to largely suppress interference patterns of the laser beam emerging from the window, the laser beam that hits the inside of the sloped window that faces the optical beam shaping element acts—as explained above—in accordance with the Brewster angle known from optical science in terms of transmission and reflection. In accordance with another embodiment, this can advantageously be further supported by an anti-reflection coating of the window of the housing of the laser diode structure. The Brewster angle indicates the angle at which only the portions of the incident and polarized light that are polarized perpendicular to the plane of incidence are reflected. It is a special feature of Brewster angle incidence that the laser beam refracted at a certain angle stands orthogonally on the reflected one. As a consequence, the entire light beam that is polarized parallel to the plane of incidence is refracted, and only the portion that is polarized perpendicular to the plane of incidence is reflected.

Preferably, the laser diode chip is arranged on a thermo element known as a Peltier element so that the beam shaping element and the laser diode chip have the temperature defined by the Peltier element. The identical temperature of the beam shaping element and the laser diode chip is achieved by the close contact between the two.

The proposed structure is not limited to VCSEL but can also be used in principle for DFBs and any other diode lasers. With DFBs, it is practical to use mirrors as beam shaping element.

According to the method proposed by the invention, for optical gas detection by means of a laser beam emitted by a laser diode structure that comprises a hermetically sealed housing with electrical connections, a bottom, and a window, with a laser diode chip and a temperature control system for the laser diode chip being provided in the housing, and with an optical beam shaping element, for example a lens, that collimates a laser beam emerging from a laser aperture of the laser diode chip prior to its passage through the window being provided between the laser diode chip and the window of the housing. After the beam shaping element, in order to reduce interference phenomena of the laser beam in the housing, the collimated laser beam is directed at the window at an angle in such a way that reflections of the passing laser beam occurring at the window are guided past a laser aperture of the laser diode chip. For this purpose, the window may either be inclined relative to a center axis of the laser beam that may extend, for example, perpendicular to the laser aperture, or, with the window arranged parallel to the laser aperture, the laser beam can be inclined relative to the window by means of suitable beam directing elements. The beam shaping element and the laser diode chip are placed in a defined temperature condition that is kept constant. This maintains a uniform defined temperature condition of the beam shaping element relative to the laser diode chip. Of special importance for the reduction of etalons due to the self-mixing of portions of the laser beam reflected back to the laser aperture, a constant temperature difference is required between the laser diode chip and the beam shaping element. For this purpose, the laser diode chip and the beam shaping element may have identical or different temperature values. Ideally, the temperature of the beam shaping element is the same as that of the laser diode chip. This can be achieved, for example, by providing a contact with good thermal transfer between the beam shaping element and the laser diode chip, for example by having the laser diode chip carry the beam shaping element. For this purpose, the beam shaping element that may be designed as described above, is preferably attached to, or formed on the laser diode chip, making contact. Ideally, the beam shaping element is arranged directly on the laser diode chip, with a boundary surface of the beam shaping element being connected without any spacing to the laser diode chip, preferably to the laser aperture of the laser diode chip.

The invention offers the advantage that because of the collimated laser beam not hitting the window perpendicularly, reflections possibly occurring on the window are not superimposed on the laser beam directed at the window so that interference phenomena of the laser beam inside the laser diode structure are reliably avoided. It also has the advantage that, due to the temperature-controlled beam shaping element that is connected with the laser diode chip in a thermally conductive way, no significant temperature differences will occur so that the beam shaping element has no negative effects on the etalons. In addition, due to a reduction of the transitions of the laser beam in the housing from an optically more dense to an optically less dense medium or vice versa, the number of reflections occurring on boundary surfaces is reduced. This significantly increases the detection limits of a gas sensor as well as its reliability compared to known laser diode structures. Also, the manufacture of a laser diode structure is cost-efficient, with the additional costs compared with conventional laser diode structures being small.

Below, the invention is explained in detail with reference to two embodiments shown in the drawing. Additional characteristics of the invention follow from the description below of the embodiments of the invention in conjunction with the claims and the attached drawing. The individual characteristics of the invention may be implemented either by themselves or in combinations of several in different embodiments of the invention. In a simplified schematic section view,

DETAILED DESCRIPTION OF THE INVENTION

Figure 1:
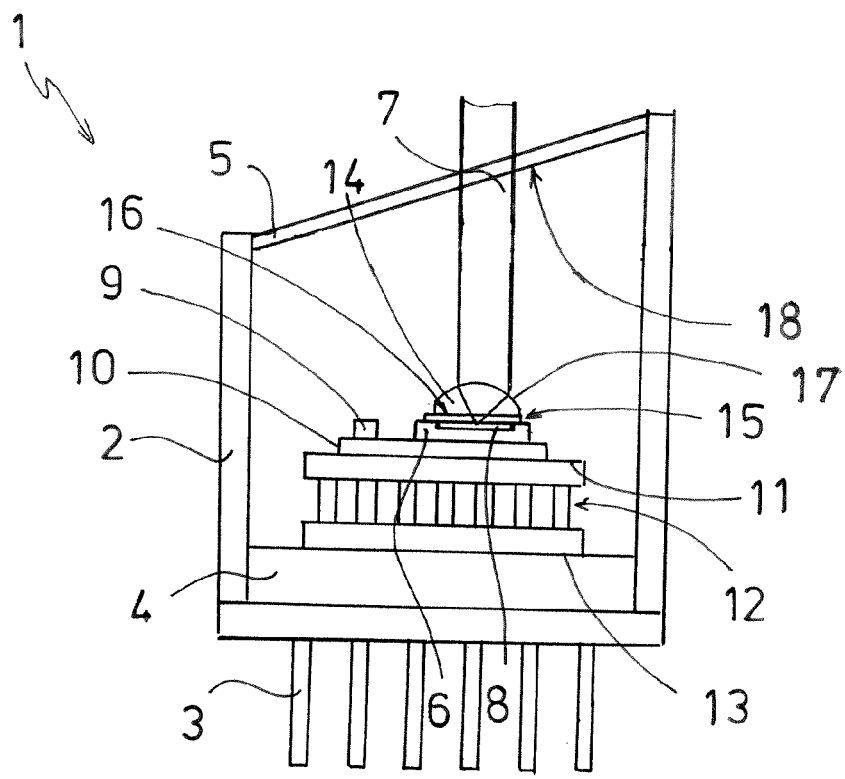
FIG. 1 shows a laser diode structure according to the invention with a spherical microlens and a window that is inclined in relation to the bottom of the housing.

FIG. 1 shows a first embodiment of a laser diode structure 1 according to the invention with a hermetically sealed housing 2 that comprises a number of electrical connections 3 on a bottom 4 of the housing 2. Opposite the bottom 4, a window 5 is provided as exit from the housing 2 for the laser beam 7 emitted by the laser diode chip 6. The window 5 extends at an angle to the bottom 4 of the housing 2 and to the laser aperture 8 of the laser diode chip 6. Together with a thermistor as thermal sensor 9, the laser diode chip 6 is glued onto a carrier 10 that, in turn, is glued to the cold flat surface 11 of a Peltier element 12. With a hot flat surface 13, the Peltier element 12 is connected to the bottom 4 of the housing 2, with the thermistor 9 regulating the current through the Peltier element 12.

A microlens 14, overlapping the laser aperture 8, for collimating the laser beam 7 is provided between the laser diode chip 6 and the window 5 of the laser diode 1. The microlens 14 is carried by the laser diode chip 6 and connected with surface-to-surface contact to the laser aperture 8 by means of a layer 15 of adhesive agent consisting of glue. As entry aperture, the microlens 14 has a plane boundary surface 16 facing the laser aperture 8, and an exit surface 17 with convex curvature directed towards the window 5 of the housing 2. Typically, the entry aperture 16 of the microlens 14 and the laser aperture 8 are offset by several 10 µm transverse to the laser beam 7. This has the effect that reflections of the laser beam 7 that may possibly occur parallel to the emitted laser beam 7, for example from an exit surface 17 of the microlens 14 that forms a boundary surface, will miss the laser aperture 8. The adhesive layer 15 is thin and has a refractory index that corresponds to that of the lens material of the microlens 14. The microlens 14 is made as a separate part from a polymer, and is mounted on the laser diode chip 6 by means of the adhesive 15 after the curing of the polymer.

Figure 2:
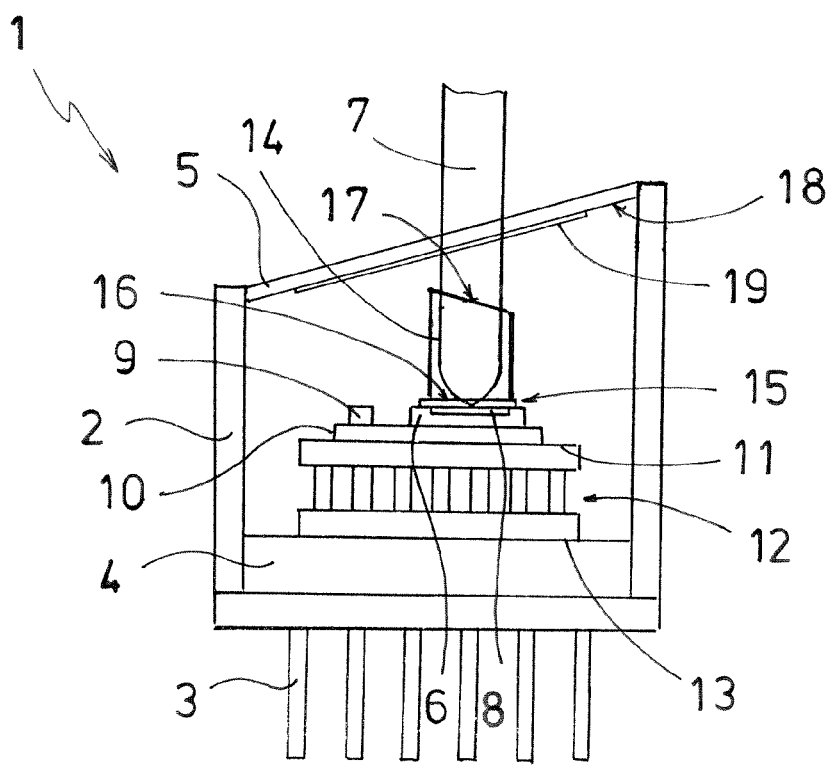
FIG. 2 shows a laser diode structure according to the invention with a sloped exit surface and a window that is inclined in relation to the bottom.

FIG. 2 shows a second embodiment of the laser diode structure 1 according to the invention. In contrast to the first embodiment shown in FIG. 1, the microlens 14 is a GRIN lens. Here, too, the window 5 of the housing 2 is inclined relative to the center axis of the laser beam 7. The inclination of the window 5 is such that reflections of the laser beam 7 in the direction of the laser diode chip 6 that may occur at the window 5 will miss the laser aperture 8. In addition, on its inside surface 18, the window 5 has an anti-reflection coating 19 that, optionally, is also possible with the laser diode structure 1 according to FIG. 1.

The GRIN lens 14 is also a convergent lens. It has a cylindrical shape and has a first plane boundary surface 16 that is associated with the laser aperture 8 and extends parallel thereto. In addition, the GRIN lens 14 has a second plane boundary surface as exit surface 17 that is associated with the window 5. The exit surface 17 is directly opposite the window 5, with the exit surface 17 being inclined relative to the center axis of the GRIN lens 14 and the window 5. In principle, however, the inclination of the exit surface 17 relative to the window 5 may be random. The boundary surface 16 of the microlens 14 implemented as a GRIN lens is connected to the laser aperture 8 with surface-to-surface contact by means of the adhesive layer 15. Other than that, the structure of this laser diode structure 1 does not differ from the structure of the laser diode structure 1 shown in FIG. 1.

The invention claimed is:

1. A gas detection laser diode structure with a hermetically sealed housing with electrical connections having a bottom and a window, with a laser diode chip and a temperature control system for the laser diode chip being provided in the housing, and with an optical beam shaping element that is arranged in physical contact with the laser diode chip and has a constant temperature condition relative to the laser diode chip and collimates a laser beam emerging from a laser aperture of the laser diode chip prior to its passage through the window being provided between the laser diode chip and the window of the housing, wherein the window of the housing is inclined relative to the center axis of the laser beam in such a way that reflections of the laser beam occurring at the window miss the laser aperture, wherein the beam shaping element is a separate part made from material that is transparent for laser light and is connected to the laser aperture optically and mechanically with at least one of a layer of a glue, a gel or a liquid comprising a material being transmissive for laser light, the material having preferably a refractory index that corresponds to the refractory index of the beam shaping element; or the beam shaping element is formed out of at least one of a polymer, a gel or a liquid directly an the laser aperture, comprising a material being transmissive for laser light; or the beam shaping element is made of a material being transmissive for laser light and is integrally formed with the laser aperture;

wherein a numerical aperture of the beam shaping element is at least as great as the laser aperture of the laser diode chip; and wherein the beam shaping element is a convex beam shaping element, and the optical axis of the beam shaping element is offset in relation to the center axis of the laser aperture.

2. A laser diode structure according to claim 1, wherein the beam shaping element is a spherical, a dome-shaped, or a rod-shaped convex microlens with a constant refractory index, or a cylindrical GRIN lens with a steadily changing refractory index.

3. A laser diode structure according to claim 1, wherein the beam shaping element is a microlens that is made from a polymer, a Sol gel, or a liquid.

4. A laser diode structure according to claim 1, wherein the beam shaping element is a diffractive optical element or a lens that is formed as part the laser diode chip.

5. A laser diode structure according to claim 1, wherein a beam shaping element implemented as a GRIN lens, the boundary surface facing away from the laser aperture is sloped.

6. A laser diode structure according to claim 1, wherein the window of the housing has an anti-reflection coating.

7. A laser diode structure according to claim 1, wherein the laser aperture is located in the focal spot of the beam shaping element and/or that the boundary surface of the beam shaping element and the laser aperture of the laser diode chip are of uniform shape and size.

8. A laser diode structure according to claim 1, wherein the temperature control system has a thermal sensor on an upper flat surface, facing a window, of a thermo element that is connected to the bottom of the housing by means of a lower flat surface.

9. A laser diode structure according to claim 1, wherein the azimuth angle of the window inclination has a fixed relationship to the polarization vector of the laser beam, and that the laser beam hitting the inside surface, facing the beam shaping element, of the window acts in accordance with Brewster's law in terms of transmission and reflection.

10. A method for optical gas detection by means of a laser beam where the laser beam is emitted by a laser diode structure that has a hermetically sealed housing with electrical connections, a bottom, and a window in which a laser diode chip and a temperature control system for the laser diode chip are located, wherein prior to passing through the window, a laser beam emitted by the laser diode chip is collimated by a beam shaping element, and after the beam shaping element, the collimated laser beam is directed at the window at an angle in such a way that reflections of the laser beam occurring at the window are directed past a laser aperture of the laser diode chip, and the beam shaping element has a defined temperature condition relative to the laser diode chip that is kept constant, wherein the beam shaping element is arranged or formed on the laser aperture of the laser diode chip in contact with the laser diode chip, and wherein the beam shaping element is a separate part made from material that is transparent for laser light and is connected to the laser aperture optically and mechanically with at least one of a layer of a glue, a gel or a liquid comprising a material being transmissive for laser light, the material having preferably a refractory index that corresponds to the refractory index of the beam shaping element; or the beam shaping element is formed out of at least one of a polymer, a gel or a liquid directly an the laser aperture, comprising a material being transmissive for laser light; or the beam shaping element is made of a material being transmissive for laser light and is initial integrally formed with the laser aperture;

a numerical aperture of the beam shaping element is at least as great as the laser aperture of the laser diode chip; and wherein the beam shaping element is a convex beam shaping element, and the optical axis of the beam shaping element is offset in relation to the center axis of the laser aperture.

* * * * *